United States Patent
Boni et al.

(10) Patent No.: US 10,004,774 B2
(45) Date of Patent: Jun. 26, 2018

(54) LOZENGE FOR TREATING SORE THROAT, HOARSENESS AND ASSOCIATED DRY COUGH, AND INFLAMMATORY DISEASES OF THE ORAL AND PHARYNGEAL CAVITY

(71) Applicant: Sanofi-Aventis Deutschland GmbH, Paris (FR)

(72) Inventors: Julia Boni, Memmingen (DE); Bernd Plohmann, Oberhoefen (DE); Sandra Sauerland, Ummendorf (DE)

(73) Assignee: SANOFI-AVENTIS DEUTSCHLAND GMBH, Paris (FR)

( * ) Notice: Subject to any disclaimer, the term of this patent is extended or adjusted under 35 U.S.C. 154(b) by 0 days. days.

(21) Appl. No.: 15/066,604

(22) Filed: Mar. 10, 2016

(65) Prior Publication Data
US 2016/0193267 A1 Jul. 7, 2016

Related U.S. Application Data

(62) Division of application No. 14/242,121, filed on Apr. 1, 2014.

(30) Foreign Application Priority Data

Apr. 2, 2013 (EP) .................................. 13161902.5

(51) Int. Cl.
| | | |
|---|---|---|
| A61K 36/185 | (2006.01) | |
| A61K 9/00 | (2006.01) | |
| A61K 36/10 | (2006.01) | |
| A61K 33/06 | (2006.01) | |
| A61K 31/351 | (2006.01) | |
| A61K 45/06 | (2006.01) | |
| A61K 36/28 | (2006.01) | |
| A61K 36/68 | (2006.01) | |
| A61K 31/7034 | (2006.01) | |
| A61K 36/062 | (2006.01) | |

(52) U.S. Cl.
CPC .......... *A61K 36/185* (2013.01); *A61K 9/0056* (2013.01); *A61K 31/351* (2013.01); *A61K 31/7034* (2013.01); *A61K 33/06* (2013.01); *A61K 36/062* (2013.01); *A61K 36/10* (2013.01); *A61K 36/28* (2013.01); *A61K 36/68* (2013.01); *A61K 45/06* (2013.01)

(58) Field of Classification Search
None
See application file for complete search history.

(56) References Cited

U.S. PATENT DOCUMENTS

2007/0178123 A1* 8/2007 Levenson ............ A61K 9/0053
424/400

FOREIGN PATENT DOCUMENTS

| EP | 2361623 A1 | 8/2011 |
| JP | 2011001321 | 1/2011 |

OTHER PUBLICATIONS

Allan (On the treatment of Hooping cough, Glasgow Medical Journal, 1880, vol. 13, p. 93-94.*
SmithKline Beechman (Trademark product Bonnington's Irish Moss product information brochure, 1996, pp. 1-2.*
Gibson, Practice of Medicine, vol. 1, Lippincott Company, London, 1901, p. 439).*
Abstract in English for JP 2011001321, Jan. 6, 2011, XP002708379.
International Search Report for corresponding application PCT/EP2014/056437, dated May 13, 2014.
TCM: Accession No. CN1569192. Ly Wenxiao, Zhong Weidong: "A kind of laryngopharynx health tea and its preparation method/A kind of new chinese medicinal composition and its preparation of medical tea, which can used for the prevention and treatment of acute/chronic pharyngolaryngitis, stomatitis and upper respiratory infection", Jan. 26, 2005, XP002708380.

* cited by examiner

*Primary Examiner* — Bethany P Barham
*Assistant Examiner* — Ping Cao
(74) *Attorney, Agent, or Firm* — Edell, Shapiro & Finnan, LLC

(57) ABSTRACT

The present invention relates to a pharmaceutical formulation containing a combination of (a) at least one astringent active substance and (b) at least one mucilaginous drug and the use thereof for the prevention or treatment of inflammatory diseases of the oropharyngeal region and for the treatment of painful irritations of the mucosa in the oropharyngeal region and associated irritable cough.

8 Claims, No Drawings

LOZENGE FOR TREATING SORE THROAT, HOARSENESS AND ASSOCIATED DRY COUGH, AND INFLAMMATORY DISEASES OF THE ORAL AND PHARYNGEAL CAVITY

The present invention relates to a pharmaceutical formulation containing a combination of (a) at least one astringent active substance and (b) at least one mucilaginous drug and the use thereof for the prevention or treatment of inflammatory diseases of the oropharyngeal cavity and for treating painful irritations of the mucosa in the oropharyngeal region and irritable cough associated therewith.

BACKGROUND TO THE INVENTION

The present invention relates to a pharmaceutical composition in the form of a formulation suitable for sucking, the composition containing a combination of at least one astringent active substance with at least one second mucilaginous drug or an extract thereof, for the treatment of, in particular, irritations and inflammatory diseases of the oropharyngeal cavity, dry mouth and cough.

The oral mucosa serves particularly to protect the underlying tissue and acts as a natural barrier against mechanical injuries (lesions) and against the penetration of microorganisms and toxic substances. It moistens the oral cavity and wets food to enable it to be digested.

The laryngeal/pharyngeal cavity is lined with a mucosa the essential component of which is the epithelium. The epithelium is the interface between the human body and ingested substances and forms a complex physicochemical barrier which, supplemented by the mucociliary apparatus, constitutes the first defence against pathogens. Mucus covers the epithelium and provides an additional protection for the mucosa, in which it forms a semi-permeable barrier that allows the exchange of nutrients, water and gases but keeps out pathogenic germs. Mucus is a viscoelastic gel of complex composition which is continuously secreted by intraepithelial cells and salivary glands. The main components of mucus are mucins, large and strongly charged glycoproteins which form the structural framework of the mucosal barrier by cross-linking.

The important factors for mucociliary clearance are the number of cilia, their structure and activity, as well as their coordinated movement. Optimum function is guaranteed at 37° C. and an absolute humidity of 44 mg/dm$^3$ (corresponding to 100% relative humidity). Cold, dry or overheated room air as well as alcohol or nicotine adversely affect the normal function of the mucosa and may lead to mucosal irritation, hoarseness, sore throat and dry cough. Under these circumstances, bacterial colonisation is promoted and pulmonary infections may result.

Often, inflammatory diseases of the oropharyngeal cavity also occur as secondary symptoms of colds and influenza-type infections. These frequently involve pain symptoms that are unpleasant for the patient and cause difficulty in swallowing. Inflammations of the oral cavity e.g., gingivitis, stomatitis or oral mucosal lesions have symptoms that are unpleasant for the patient affected.

Typically, inflammatory diseases of the oropharyngeal cavity are treated by topical therapy, for example in the form of mouth and throat rinses, sprays or lozenges. In serious cases systemic therapy is additionally given, e.g. by administering antibiotics.

In particular, 1-hexadecylpyridinium chloride (international generic name: cetylpyridinium chloride (CPC)) has proved useful for the topical treatment of inflammatory diseases of the oropharyngeal region. It is a quaternary ammonium compound with a bactericidal and fungicidal activity which is used in lozenges, for example. A disadvantage of this active substance is the fact that at high doses and if consumed to excess it may cause gastrointestinal problems, breathing difficulties and increased methaemoglobin formation, particularly in children.

Additionally, 1,3-bis(2-ethylhexyl)-hexahydro-5-methyl-5-pyridinamine (international generic name: hexetidine) has also proved useful as a topical antiseptic or disinfectant for the oral, laryngeal and pharyngeal mucosa and is administered for example as a spray or in the form of mouthwashes or gargling solutions. When used long-term or in high doses, once again gastrointestinal disorders may result or there may be gustatory irritations.

Other active substances for the topical treatment of inflammatory processes of the oropharyngeal cavity are astringent active substances, particularly potassium aluminium sulphate decahydrate (international generic name: alum). This is a salt that is traditionally used to treat injuries in the mouth, gingivitis or mucosal swellings and bleeding. As a result of its astringent effect it also reduces colonisation by germs and can alleviate pain by its effect of reducing swelling. A disadvantage is the feeling of a dry mouth caused by the astringent effect.

Active substances of natural origin are also used, such as so-called mucilaginous drugs or extracts thereof such as for example Icelandic moss (*Lichen Islandicus*). These mucilaginous drugs contain a high concentration of polysaccharides which form mucilages when combined with water. Used for inflammatory diseases of the oropharyngeal cavity in the form of e.g. lozenges or sprays, they form a protective layer and moisten the mucosa. This additional layer of mucus protects the sensitive mechanical and chemical receptors in the mucosa from external irritations and thereby reduces irritations such as for example scratchiness, hoarseness and irritable cough. Generally, these active substances are used in the form of monopreparations, but do not always achieve the desired success.

The problem of the present invention is, therefore, to provide a pharmaceutical preparation in the form of a solid formulation for the topical treatment of inflammatory diseases of the oropharyngeal region which should at least substantially prevent or reduce the disadvantages of the prior art described above.

The Applicant has now surprisingly found that the problem mentioned above is solved by formulating a pharmaceutical preparation in the form of a fixed dosage of at least one astringent active substance (e.g. alum) with at least one mucilaginous drug and/or an extract thereof (e.g. Icelandic moss). A composition of this kind is particularly suitable in the form of lozenges, produced by compression of powder mixtures or based on hard caramels which may be used for topical application in cases of painful or inflammatory and painful diseases of the oropharyngeal cavity.

SUBJECT-MATTER OF THE INVENTION

The present invention relates to a pharmaceutical formulation containing a combination of (a) at least one astringent active substance and (b) at least one mucilaginous drug.

The above-mentioned combination is particularly suitable for the prevention and treatment, particularly for the symptomatic prevention or treatment, of inflammatory diseases of the oropharyngeal cavity. The above-mentioned combination is also suitable for the temporary sole or supplementary treatment of the above-mentioned diseases.

Consequently, the present invention further relates to the use of the pharmaceutical formulation according to the invention for the prevention or treatment of inflammatory diseases of the oropharyngeal cavity.

Similarly, the present invention relates to the use of the pharmaceutical formulation according to the invention for the treatment of painful irritations of the mucosa in the oropharyngeal region and irritable cough associated therewith.

Similarly, the present invention relates to the combination according to the invention of (a) at least one astringent active substance and (b) at least one mucilaginous drug, and their use in the prevention or treatment of inflammatory diseases of the oropharyngeal cavity, and/or their use in the treatment of painful irritations of the mucosa in the oropharyngeal region and irritable cough associated therewith.

The use of the combination according to the invention based on at least one astringent active substance and at least one mucilaginous drug results in a preparation which, in addition to being highly effective, is well-tolerated and from which side effects are largely absent.

The principle of activity of the composition according to the invention is based on purely physical or physicochemical processes. The fundamental principle of the present invention is based on a controlled combination of astringent active substances on the one hand and active substance components based on mucilaginous drugs on the other hand, while the inventors have discovered that the effectiveness of astringent active substances on the one hand and mucilaginous drugs on the other hand, in respect of the diseases mentioned above, is unexpectedly increased by the combination according to the invention.

DESCRIPTION

The term "combination" as used herein describes at least two active substances selected from among (a) astringent active substances and (b) mucilaginous drugs, which are present in a ratio to one another that is suitable for taking them together.

The term "mucilaginous drug" as used herein encompasses the mucilaginous drugs, the constituents and extracts thereof. Thus, for example, the term "Icelandic moss" as used herein encompasses Icelandic moss, its constituents and its extracts.

Mucilaginous drugs used according to the invention that have proved particularly suitable are Icelandic moss (*Lichen islandicus*), common mallow (*Malva sylvestris*), lance leaf plantain (*Plantago lanceolata*), marshmallow (*Althaea officinalis*) and coltsfoot (*Tussilago farfara*) and the mixtures thereof. Preferably, Icelandic moss is used, particularly in the form of an extract.

The term "astringent active substance" as used herein comprises active substances which have a drying, haemostatic and anti-inflammatory activity when they come into contact with the skin or mucosa as a result of protein precipitation. In particular, alum, tannin, policresulen and silver nitrate or mixtures thereof are suitable as astringent active substances. Preferably, alum is used.

One particular embodiment of the present invention relates to a pharmaceutical formulation according to one of the preceding claims comprising (a) at least one astringent active substance; (b) at least one mucilaginous drug and (c) at least one other adjuvant.

The term "pharmaceutical formulation" as used herein comprises in particular conventional solid pharmaceutical formulations such as lozenges, prepared for example by powder compression or based on hard caramels.

Suitable adjuvants are in particular tabletting excipients and fillers, for example isomalt, fructose and/or glucose syrup, silicon dioxide, talc, magnesium stearate, macrogol, polydextrose or xanthan gum, sweeteners, for example sugar substitutes, particularly isomalt, sorbitol, polydextrose, maltitol or isomaltitol, sweeteners, for example aspartame, acesulfame, cyclamate, saccharin or xylitol, flavourings, colourings and/or stabilisers, for example tartaric acid or citric acid.

The proportion by weight of the adjuvants used is normally in the range from 50 to 99.5% by weight, preferably from 75 to 99% by weight, particularly preferably from 85 to 95% by weight, based in each case on the total weight of the pharmaceutical formulation.

In a particular embodiment of the pharmaceutical formulation according to the invention, Icelandic moss is used as the mucilaginous drug. Icelandic moss is preferably used as an extract.

Suitable extracts of Icelandic moss are obtained for example by aqueous, alcoholic or aqueous-alcoholic extraction and optionally subsequent drying. These extracts normally consist primarily of the mucilage-forming polysaccharides lichenin and isolichenin. The increased content of mucilages improves the therapeutic effect compared with the pure drug. Besides the mucilages the extract contains lichen acids which have a slight antimicrobial effect. Compared with the drug, the processing of the extracts is easier.

In one particular embodiment of the pharmaceutical formulation according to the invention, mallow is used as the mucilaginous drug. Mallow is preferably used here as an extract.

Suitable extracts of mallow are obtained for example by aqueous, alcoholic or aqueous-alcoholic extraction and optionally subsequent drying. These extracts usually consist mainly of mucilages. The latter are made up of the cross-linked individual components glucose, arabinose, rhamnose and galactose. The content in the extract is many times higher than in the pure drug, thus improving the therapeutic effect.

The pharmaceutical formulation according to the invention usually contains the mucilaginous drug in an amount of 1 mg to 500 mg, preferably 10 mg to 250 mg, particularly preferably 50 mg to 200 mg.

The proportion by weight of the mucilaginous drug used is normally in the range from 1 to 50% by weight, preferably 2 to 25% by weight, particularly preferably 5 to 10% by weight, based in each case on the total weight of the pharmaceutical formulation.

In one particular embodiment of the pharmaceutical formulation according to the invention, alum is used as the astringent active substance.

In another particular embodiment of the pharmaceutical formulation according to the invention, tannin is used as the astringent active substance.

The pharmaceutical formulation according to the invention normally contains the astringent active substance in an amount of 0.1 mg to 50 mg, preferably from 0.5 mg to 20 mg, particularly preferably from 1 mg to 10 mg.

The proportion by weight of the astringent active substance used is normally in the range from 0.01 to 5% by weight, preferably 0.05 to 2% by weight, particularly preferably 0.1 to 1% by weight, based in each case on the total weight of the pharmaceutical formulation.

A preferred embodiment of the present invention relates to the combination of Icelandic moss as mucilaginous drug and alum as astringent active substance.

Icelandic moss is normally used in an amount of 1 mg to 500 mg, preferably in an amount of 10 mg to 250 mg, particularly preferably in an amount of from 50 mg to 200 mg.

Alum is conventionally used in an amount of 0.1 mg to 20 mg, preferably in an amount of 1 mg to 15 mg, particularly preferably in an amount of 3 to 10 mg.

The ratio by weight of Icelandic moss to alum is usually in the range from 5:1 to 50:1, preferably from 10:1 to 25:1, particularly preferably from 15:1 to 20:1.

The proportion by weight of Icelandic moss and alum is usually in the range from 0.5 to 50% by weight, preferably from 1 to 25% by weight, particularly preferably from 5 to 15% by weight, based in each case on the total weight of the pharmaceutical formulation.

The pharmaceutical formulation according to the invention is preferably prepared as a lozenge. Suitable lozenges may be produced for example by powder compression or based on hard caramels.

The total weight of the pharmaceutical formulation is conventionally in the range from 500 mg to 5000 mg, preferably from 750 mg to 4000 mg, particularly preferably from 1000 mg to 3000 mg.

The pharmaceutical formulation according to the invention is usually administered up to 20 times a day, preferably up to 12 times, particularly preferably up to 8 times a day.

The combination according to the invention is suitable for the prevention or treatment of inflammatory diseases of the oropharyngeal cavity. Accordingly, the pharmaceutical formulation according to the invention is also suitable for this use.

The combination according to the invention is particularly suitable for the prevention or treatment of inflammatory diseases of the oropharyngeal cavity that are painful or accompanied by pain. Accordingly, the pharmaceutical formulation according to the invention is also suitable for this use.

The combination according to the invention is particularly also suitable for the symptomatic treatment of inflammatory diseases of the oropharyngeal cavity. Accordingly, the pharmaceutical formulation according to the invention is also suitable for this use.

The combination according to the invention is particularly also suitable for the treatment of inflammation and/or pain in inflammatory diseases of the oropharyngeal cavity. Accordingly, the pharmaceutical formulation according to the invention is also suitable for this use.

The combination according to the invention is particularly also suitable for the treatment of irritable cough, particularly in inflammatory diseases of the oropharyngeal cavity. Accordingly, the pharmaceutical formulation according to the invention is also suitable for this use.

The combination according to the invention is particularly also suitable for the treatment of difficulty in swallowing, particularly in inflammatory diseases of the oropharyngeal cavity. Accordingly, the pharmaceutical formulation according to the invention is also suitable for this use.

The combination according to the invention is particularly also suitable for restoring the voice that has been affected by hoarseness and pain, particularly in inflammatory diseases of the oropharyngeal cavity. Accordingly, the pharmaceutical formulation according to the invention is also suitable for this use.

The combination according to the invention is particularly suitable for the topical administration of the active substances. Accordingly, the pharmaceutical formulation according to the invention is also suitable for this use.

The combination according to the invention is also particularly suitable for the treatment of painful irritations of the mucosa in the oropharyngeal cavity and associated irritable cough. Accordingly, the pharmaceutical formulation according to the invention is also suitable for this use.

The combination according to the invention helps to soothe the irritated and/or inflamed oropharyngeal cavity and alleviates sore throat.

The combination according to the invention helps to regenerate the mucosa in the presence of symptoms caused by colds.

The combination according to the invention helps in the treatment of sore throat.

The combination according to the invention helps to alleviate the symptoms of throat inflammations and irritations, such as a dry, itchy or scratchy throat.

The combination according to the invention helps to protect the throat from further irritation.

The combination according to the invention acts as a protective film for the irritated mucosa to prevent bacterial colonisation.

The combination according to the invention soothes the oropharyngeal cavity and thus helps to break the cycle of sore throat and dry cough.

The combination according to the invention helps to reduce the symptoms of dry cough and alleviates cough irritation.

The combination according to the invention helps to soothe and moisten the throat and thus alleviates cough.

The combination according to the invention helps with difficulties in swallowing.

The combination according to the invention helps with hoarseness.

Another particular subject-matter of the present invention relates to the combination of (a) at least one astringent active substance and (b) at least one mucilaginous drug for use in the prevention or treatment of inflammatory diseases of the oropharyngeal cavity.

Another particular subject-matter of the present invention relates to the combination of (a) at least one astringent active substance and (b) at least one mucilaginous drug for use in the treatment of painful irritations of the mucosa in the oropharyngeal cavity and associated irritable cough.

EXAMPLES

1. Production Examples

Production of pharmaceutical preparations according to the invention in the form of lozenges based on an astringent active substance in conjunction with different mucilaginous drugs.

Various compositions are produced in the form of lozenges based on powder compression or based on hard caramels. For the compressed lozenges, sugar substitutes, particularly isomalt, sorbitol or polydextrose may preferably be used, for the hard sweet base fructose and/or glucose syrup may be used, as sugar-free alternative sugar substitutes, particularly sugar alcohols, preferably maltitol or isomaltitol, may be used. Variable amounts of sweeteners (e.g. aspartame, acesulfame, cyclamate, saccharin or xylitol) may be added. Other excipients and active substances are incorporated in the matrix and the lozenges are produced by the production method known per se.

In the case of the compressed powder mixtures, the excipients are weighed in accordance with the recipe and mixed with the matrix. In the case of liquid excipients or active substances, these may be added by means of a further granulating step. Then powder or granules are compressed to form lozenges. The excipients or active substances may be compressed jointly or separately, as selected, in one or more layers (1-, 2- or 3-layered tablets).

In the case of hard caramels the raw materials are mixed according to the recipe and mixed into the heated hard caramel base. Heat-sensitive excipients and/or active substances, particularly mucilaginous drugs, preferably Icelandic moss
astringent active substances, preferably alum
optionally flavourings
optionally colourings
optionally stabilisers, particularly tartaric acid or citric acid are added in another step shortly before the final mixing and formation of the lozenges.

Using these methods, sugar-free lozenges containing different amounts of astringent active substances and mucilaginous drugs are produced, for example, as illustrated in the following Tables:

TABLE 1

1-layer lozenge produced by powder compression with 5 mg Alum and 80 mg Icelandic moss extract

| Raw materials | Amount per lozenge [mg] |
| --- | --- |
| isomalt | 1200 |
| silicon dioxide | 8 |
| lemon flavouring | 30 |
| menthol | 2 |
| talc | 50 |
| macrogol | 25 |
| alum | 5 |
| Icelandic moss extract (drug/extract 1:1.5-2.5) | 80 |
| Total | 1400 |

TABLE 2

1-layer lozenge produced by powder compression with 1 mg tannin and 150 mg mallow extract

| Raw materials | Amount per lozenge [mg] |
| --- | --- |
| Polydextrose | 1100 |
| silicon dioxide | 10 |
| strawberry flavouring | 30 |
| menthol | 4 |
| magnesium stearate | 25 |
| sucralose | 5 |
| tannin | 1 |
| mallow extract (drug/extract 4:1) | 150 |
| Total | 1325 |

TABLE 3

2-layer lozenge produced by powder compression with 5 mg alum and 80 mg Icelandic moss extract

| Raw materials | Amount per layer of lozenge - layer 1 [mg] | Amount per layer of lozenge - layer 1 [mg] |
| --- | --- | --- |
| sorbitol | 590 | 490 |
| silicon dioxide | 3 | 3 |
| strawberry flavouring | 15 | 15 |
| eucalyptus flavouring | 2 | 2 |
| talc | 25 | 25 |
| macrogol | 10 | 10 |
| xanthan gum | — | 25 |
| alum | — | 5 |
| Icelandic moss extract (drug/extract 1:1.5-2.5) | — | 80 |
| Total | | 1300 |

TABLE 4

Lozenge based on hard caramels containing 5 mg alum and 80 mg Icelandic moss extract

| Raw materials | Amount per lozenge [mg] |
| --- | --- |
| isomalt | 2500 |
| peach flavouring | 15 |
| menthol | 0.5 |
| citric acid | 35 |
| sucralose | 1.5 |
| alum | 5 |
| Icelandic moss liquid extract (drug/extract 1:1.5-2.5) | 80 |
| water | 53 |
| Total | 2960 |

2. Examples of Use 30 patients with painful irritation of the mucosa in the oropharyngeal region and in some cases with an associated irritable cough were treated with the lozenges described in the foregoing Production Examples with no additional systemic therapy. 10 patients were treated with the preparation described in Table 4, with up to six tablets being administered over a period of three days (group A). Another 10 were treated with a standard commercial preparation with only alum (9 mg per lozenge) for three days with up to six tablets (group B). Another 10 patients were given a standard commercial monopreparation with Icelandic moss (80 mg of Icelandic moss extract per lozenge) according to a similar treatment plan (group C).

Whereas all the symptoms caused by the inflammations of the oral and pharyngeal mucosa were alleviated using the formulation according to the invention, only individual complaints were alleviated with the preparations in groups B and C.

With the non-novel preparation in group B, an improvement was observed in the symptoms of inflammation and pain of the mucosa. Little to no improvement was observed in group B in the symptoms of hoarseness and dry mouth and the irritable cough associated therewith.

In the therapy with the non-novel preparation of group C an improvement was observed primarily in the irritable cough associated with inflammations of the oral and pharyngeal mucosa, dryness of the mouth and difficulty in swallowing.

The investigations demonstrate a significantly increased therapeutic success by treatment with the formulation according to the invention. Using the combination of astringent active substance and mucilaginous drug, a significant alleviation of the irritable cough as well as the symptoms of inflammation and pain took place in the patients treated with the composition according to the invention after only a short period of treatment. A rapid alleviation of the difficulty in swallowing was achieved by the application and there was a rapid restoration of voices that had been restricted by hoarseness and pain. In addition, the patients found the sucking sensation of the composition according to the invention to be very pleasant. In the improvement to the symptoms described hereinbefore, the composition according to the invention has a crucial advantage over non-novel monopreparations.

The invention claimed is:

1. A method for the treatment of inflammatory diseases of the oropharyngeal cavity which comprises the administration of a pharmaceutical composition in the form of a lozenge, the pharmaceutical composition comprising:
   at least one astringent active substance comprising alum, wherein the astringent active substance is present in an amount of no greater than 10 mg and is further present in an amount of 0.1% to 1% by weight of the pharmaceutical composition; and
   at least one mucilaginous drug comprising Icelandic moss, wherein the mucilaginous drug is present in an amount of 50 mg to 200 mg;
   wherein a ratio by weight of Icelandic moss to alum is from 15:1 to 20:1.

2. The method according to claim 1, wherein the condition to be treated includes irritable cough.

3. The method according to claim 1, wherein the condition to be treated includes difficulty in swallowing.

4. The method according to claim 1, wherein the condition to be treated includes hoarseness.

5. The method according to claim 1, wherein the condition to be treated includes pain.

6. The method according to claim 1, wherein the pharmaceutical composition, consists of (a) the at least one astringent active substance; (b) the at least one mucilaginous drug and (c) at least one further adjuvant.

7. The method according to claim 1, wherein the astringent active substance is further selected from among tannin, policresulen and silver nitrate.

8. The method according to claim 7, wherein the astringent active substance consists of alum.

* * * * *